(12) United States Patent
Mather et al.

(10) Patent No.: US 7,766,207 B2
(45) Date of Patent: Aug. 3, 2010

(54) ARTICULATING CURVED CUTTER STAPLER

(75) Inventors: Michael T. Mather, Mason, OH (US); Michael L. Kruszynski, Loveland, OH (US); Richard F. Schwemberger, Cincinnati, OH (US); Michael A. Parker, Franklin, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/511,490

(22) Filed: Aug. 29, 2006

(65) Prior Publication Data

US 2007/0039996 A1    Feb. 22, 2007

Related U.S. Application Data

(63) Continuation-in-part of application No. 11/014,910, filed on Dec. 20, 2004.

(60) Provisional application No. 60/532,912, filed on Dec. 30, 2003.

(51) Int. Cl.
*A61B 17/068* (2006.01)
*F16C 11/06* (2006.01)
*F16D 11/06* (2006.01)

(52) U.S. Cl. .................. 227/175.1; 227/9; 227/178.1; 227/181.1; 227/182.1; 403/55; 403/56; 403/90

(58) Field of Classification Search .............. 227/175.1, 227/178.1, 181.1, 182.1, 8, 19; 403/55, 56, 403/90
See application file for complete search history.

(56) References Cited

U.S. PATENT DOCUMENTS

| | | | | |
|---|---|---|---|---|
| 4,354,628 A | * | 10/1982 | Green | 227/19 |
| 4,402,444 A | * | 9/1983 | Green | 227/19 |
| 4,566,620 A | * | 1/1986 | Green et al. | 227/19 |
| 4,573,622 A | * | 3/1986 | Green et al. | 227/19 |
| 4,606,343 A | * | 8/1986 | Conta et al. | 227/178.1 |
| 4,788,978 A | * | 12/1988 | Strekopytov et al. | 227/176.1 |
| 5,020,933 A | * | 6/1991 | Salvestro et al. | 403/90 |
| 5,042,707 A | * | 8/1991 | Taheri | 606/213 |
| 5,348,259 A | * | 9/1994 | Blanco et al. | 248/276.1 |
| 5,431,323 A | * | 7/1995 | Smith et al. | 227/177.1 |
| 5,452,836 A | * | 9/1995 | Huitema et al. | 227/176.1 |
| 5,484,451 A | * | 1/1996 | Akopov et al. | 606/139 |
| 5,497,933 A | * | 3/1996 | DeFonzo et al. | 227/175.1 |
| 5,609,285 A | * | 3/1997 | Grant et al. | 227/179.1 |
| 5,632,433 A | * | 5/1997 | Grant et al. | 227/179.1 |
| 5,669,544 A | * | 9/1997 | Schulze et al. | 227/176.1 |
| 5,673,841 A | * | 10/1997 | Schulze et al. | 227/175.1 |
| 5,713,505 A | * | 2/1998 | Huitema | 227/179.1 |
| 5,732,871 A | * | 3/1998 | Clark et al. | 227/175.1 |
| 5,743,456 A | * | 4/1998 | Jones et al. | 227/176.1 |

(Continued)

FOREIGN PATENT DOCUMENTS

WO    WO 01/91646    12/2001

*Primary Examiner*—Rinaldi I. Rada
*Assistant Examiner*—Gloria R. Weeks

(57) ABSTRACT

An articulating surgical stapler having a proximal end and a distal end includes a handle at the proximal end and an end effector at the distal end for selective articulation to improve access to tissue requiring treatment and ease of use of the present linear surgical stapler. A support shaft connects the handle to the end effector. An articulation mechanism is positioned between the support shaft and the end effector permitting selective movement of the end effector relative to the support shaft.

6 Claims, 12 Drawing Sheets

U.S. PATENT DOCUMENTS

| | | | |
|---|---|---|---|
| 5,797,536 A * | 8/1998 | Smith et al. | 227/175.1 |
| 5,855,311 A * | 1/1999 | Hamblin et al. | 227/176.1 |
| 5,964,394 A * | 10/1999 | Robertson | 227/176.1 |
| 6,050,472 A * | 4/2000 | Shibata | 227/175.2 |
| 6,491,273 B2 * | 12/2002 | King et al. | 248/276.1 |
| 6,644,532 B2 * | 11/2003 | Green et al. | 227/176.1 |
| 6,767,153 B1 * | 7/2004 | Holbrook | 403/56 |
| 6,830,174 B2 * | 12/2004 | Hillstead et al. | 227/175.1 |
| 2004/0232201 A1 * | 11/2004 | Wenchell et al. | 227/176.1 |
| 2005/0113821 A1 | 5/2005 | Pendekanti et al. | |
| 2006/0011699 A1 * | 1/2006 | Olson et al. | 227/180.1 |
| 2006/0016853 A1 * | 1/2006 | Racenet | 227/176.1 |

* cited by examiner

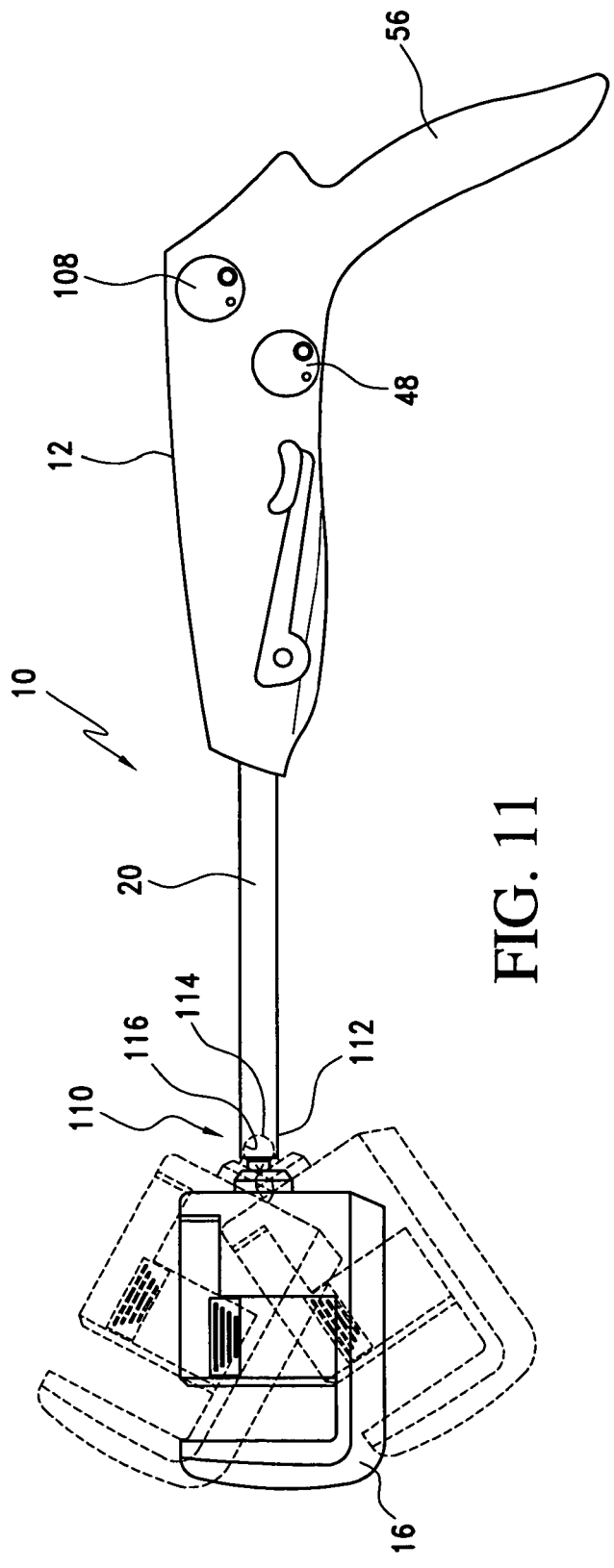
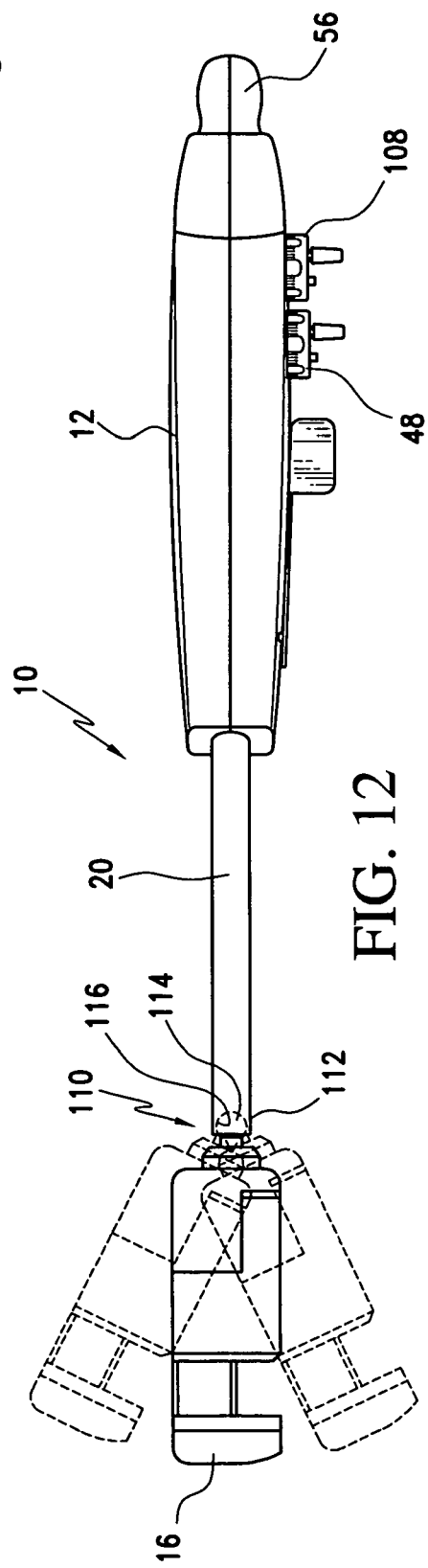

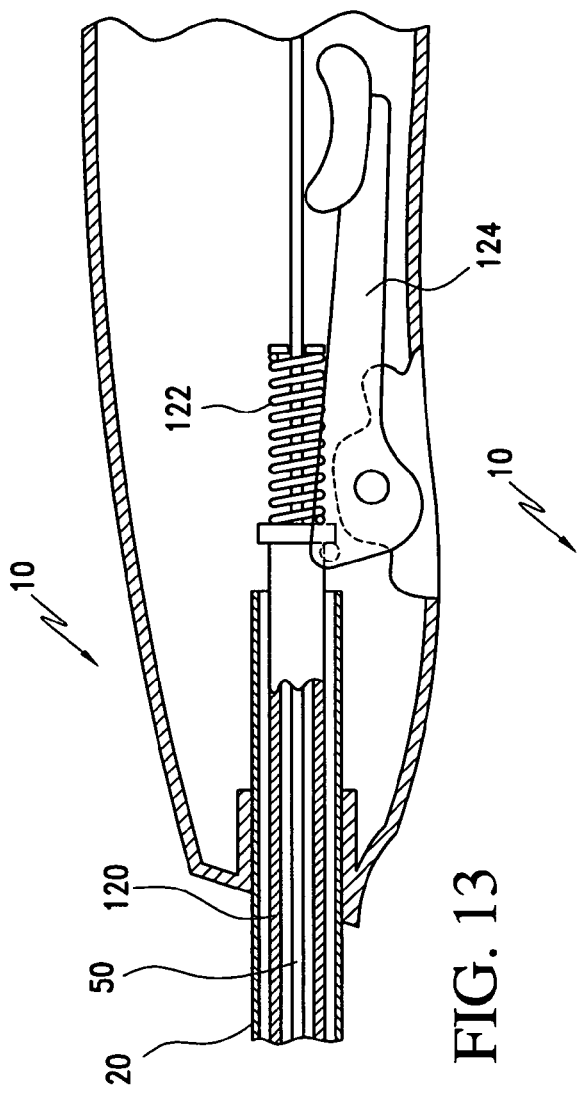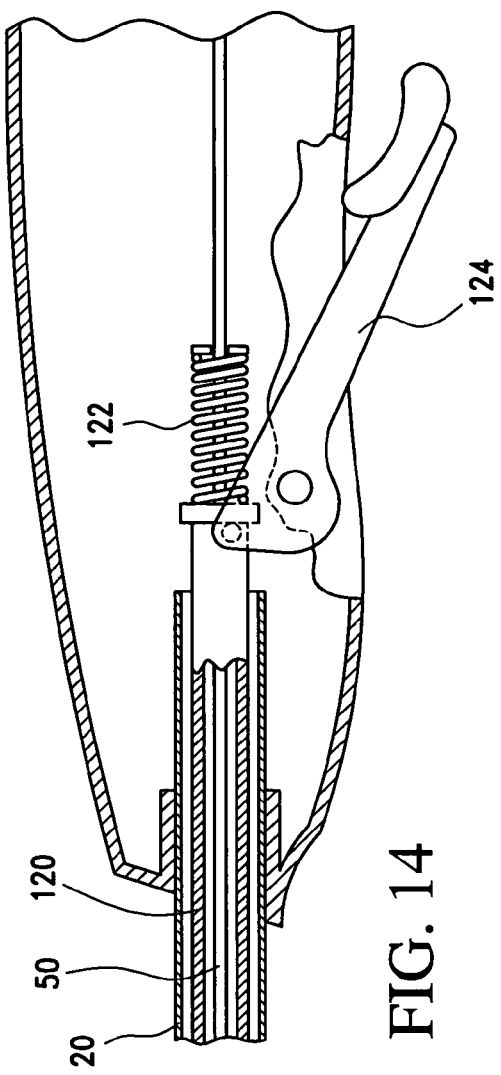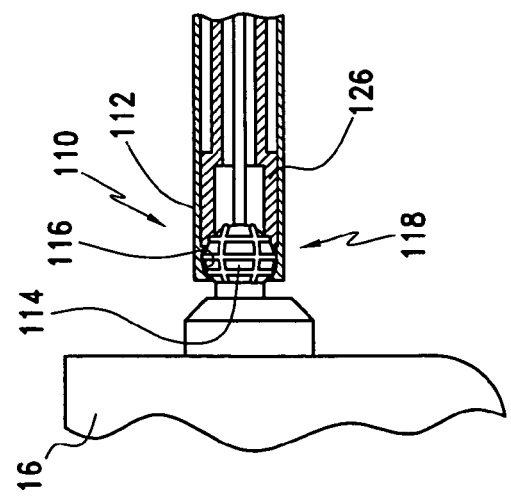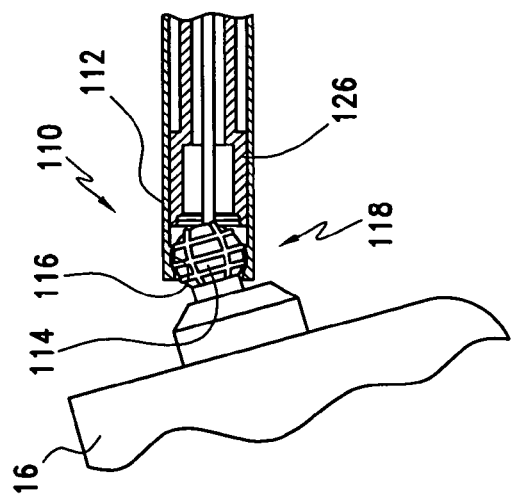
FIG. 13
FIG. 14

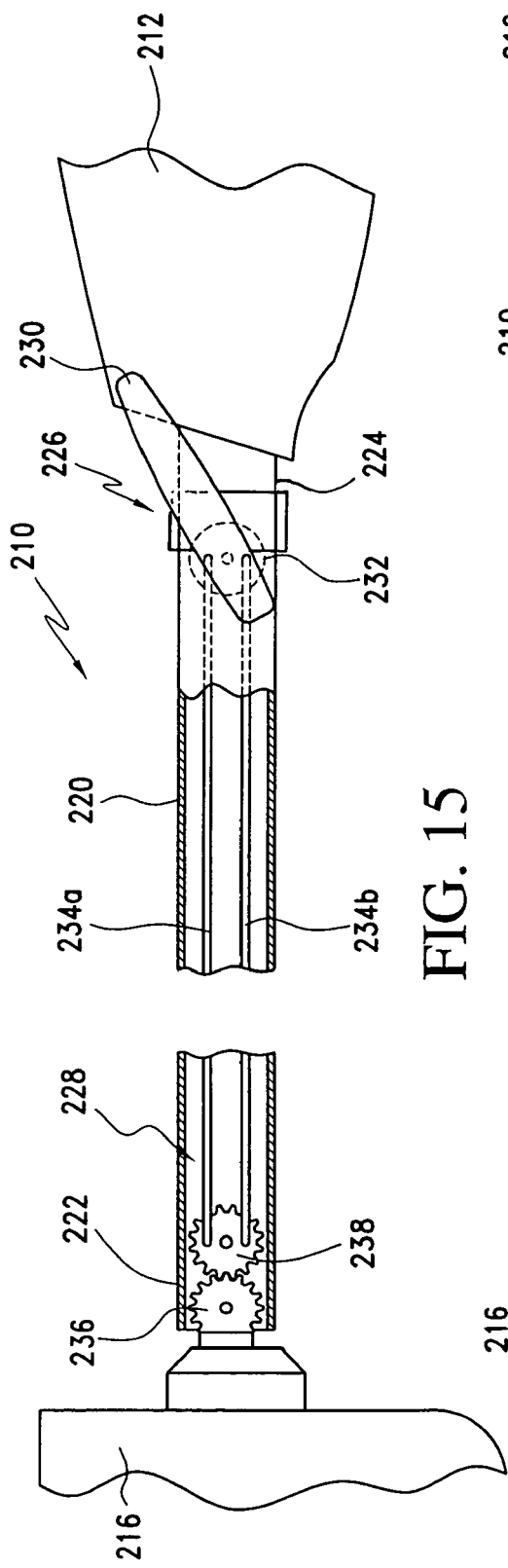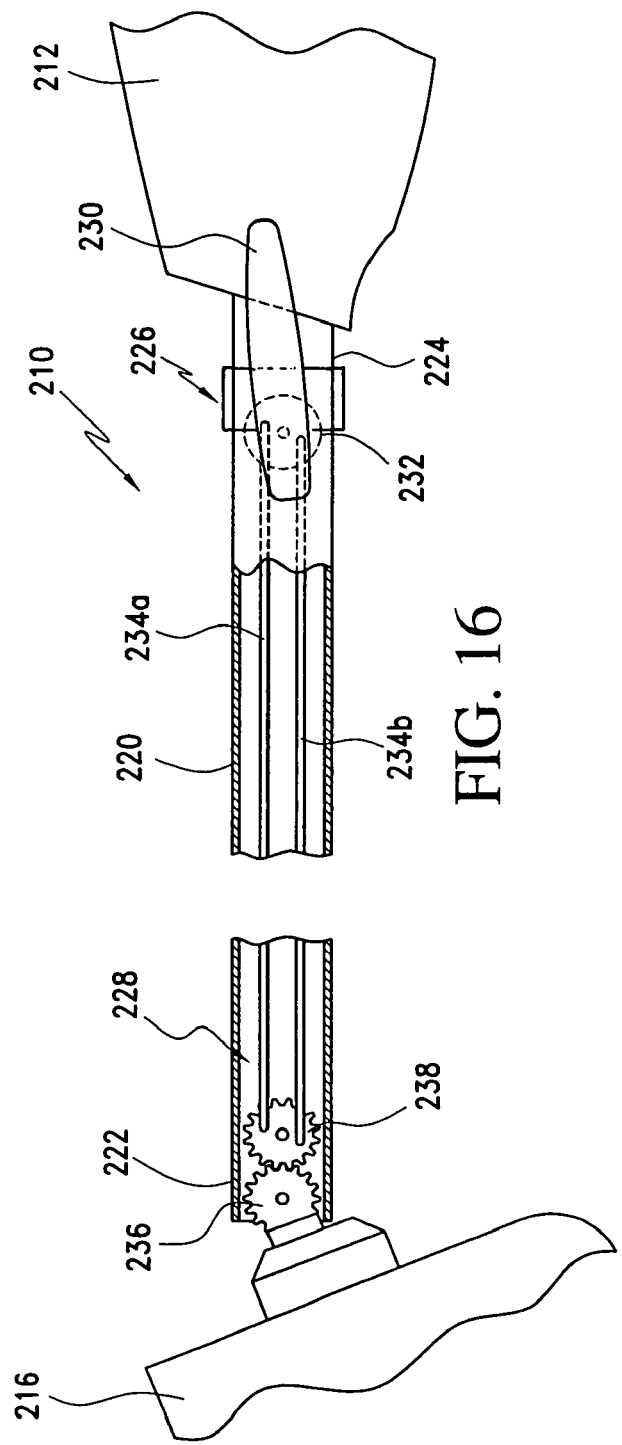

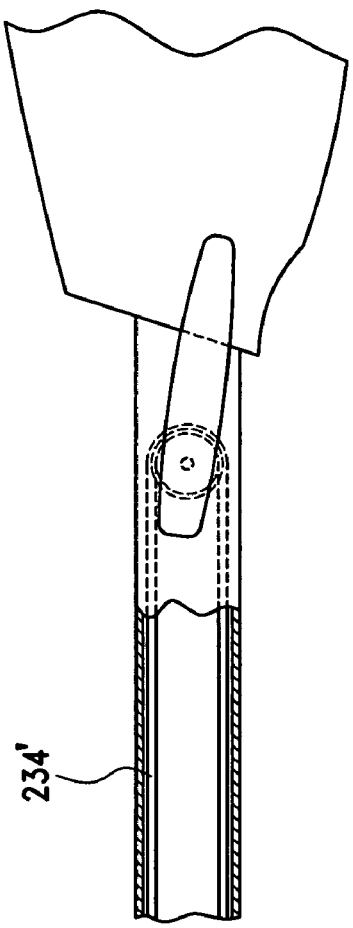
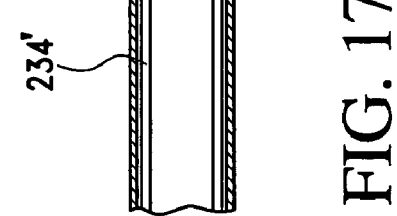
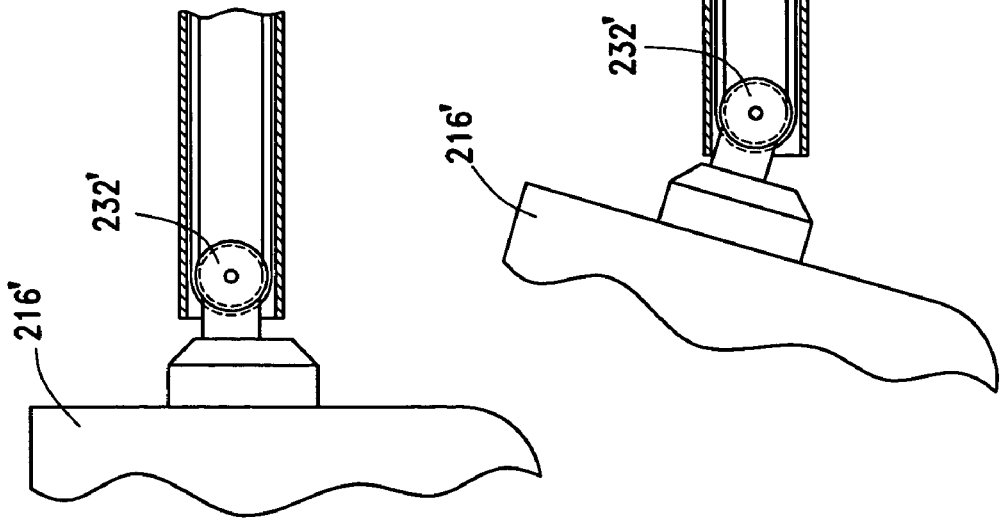

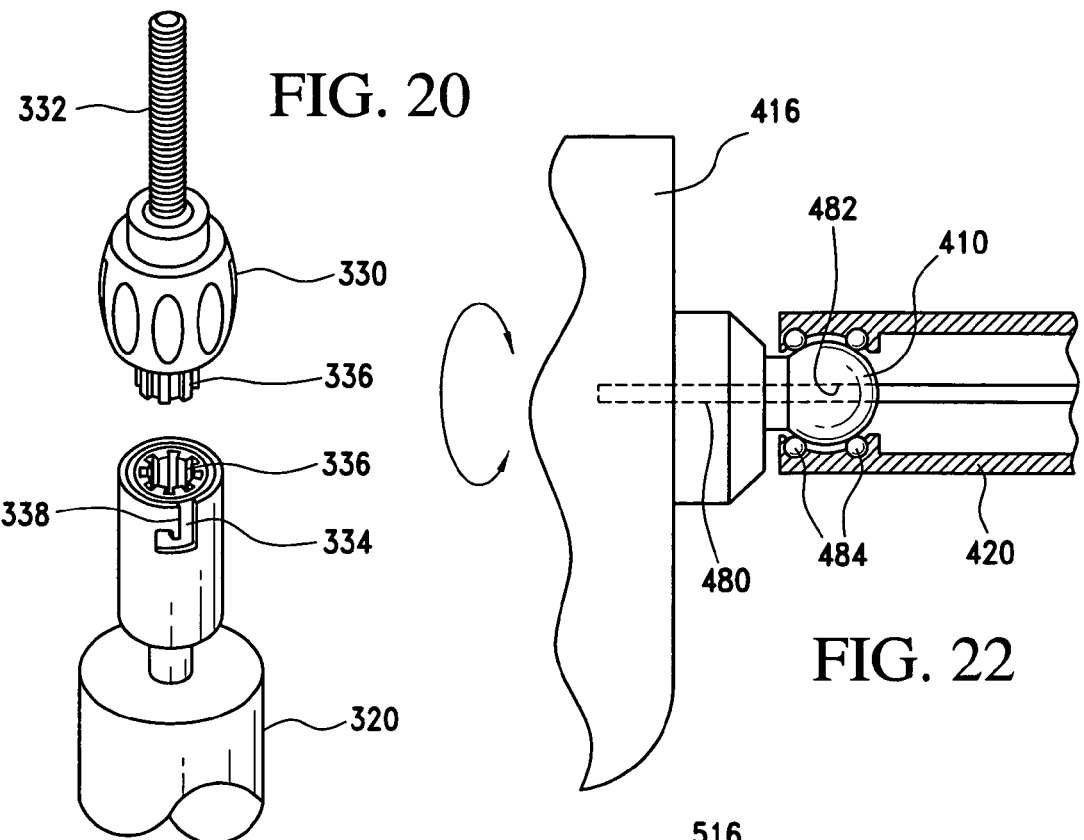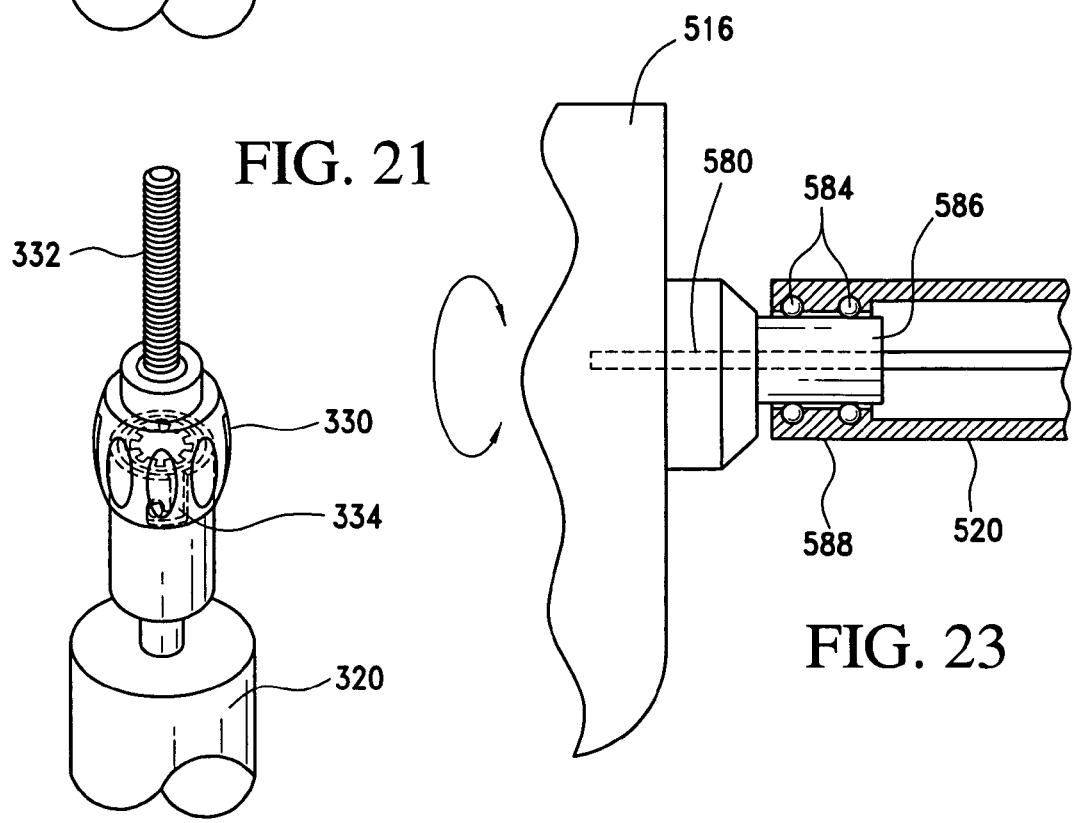

ARTICULATING CURVED CUTTER STAPLER

CROSS REFERENCE TO RELATED APPLICATIONS

This application is a continuation-in-part of U.S. patent application Ser. No. 11/014,910, filed Dec. 20, 2004, entitled "CURVED CUTTER STAPLER SHAPED FOR MALE PELVIS", which is currently pending, which claims priority of U.S. Provisional Application Ser. No. 60/532,912, entitled "CURVED CUTTER STAPLER SHAPED FOR MALE PELVIS", filed Dec. 30, 2003.

BACKGROUND OF THE INVENTION

1. Field of the Invention

The present invention relates to a surgical stapling and cutting instrument adapted for use in the diagnosis and therapy of pathologies treated by stapled resection. More particularly, the present invention relates to a surgical stapling and cutting instrument offering articulation of the end effector permitting improved access to surgical sites.

2. Description of the Prior Art

Surgical stapling and cutting instruments are commonly utilized in the diagnosis and treatment of pathologies treated by staple resection. Surgical stapling instruments provide a mechanism to extend the transluminal exploitation of mechanical suturing devices introduced via the anal canal, mouth, stomach and service accesses. Although surgical stapling and cutting instruments are most commonly utilized with rectal pathologies, surgical stapling and cutting instruments may be used in a variety of environments.

Over time, surgical stapling and cutting instruments have been developed. These instruments generally include a support frame, an anvil attached to the support frame and a cartridge module carrying a plurality of staples. The instruments also include a driver within the cartridge module which pushes all of the staples out simultaneously into the anvil to form the staples into a generally B-shape, suturing tissue together. In addition, these instruments include approximation mechanisms for moving the cartridge module from a spaced position relative to the anvil to accept tissue therebetween to a closed position where the tissue is clamped between the anvil and the cartridge module. Finally, the instruments include a firing means for moving the staple driver forward to form the staples against the anvil.

Once the instrument is positioned within the body cavity, it is imperative that the end effector be oriented properly relative to the tissue requiring resection. Generally, this is accomplished by reorienting the entire instrument, that is, the handle, shaft and end effector as they are rigidly connected along the longitudinal axis of the instrument. This, however, limits the potential for reorienting the end effector as orientation thereof is limited by the access opening through which the surgical stapling and cutting instrument is inserted within the body.

As such, a need exists for a surgical stapling and cutting instrument which provides for reorientation of the end effector without requiring reorientation of the handle and shaft extending from the body orifice. The present invention provides such a mechanism.

SUMMARY OF THE INVENTION

It is, therefore, an object of the present invention to provide an articulating surgical stapler having a proximal end and a distal end. The stapler includes a handle at the proximal end and an end effector at the distal end for selective articulation to improve access to tissue requiring treatment and ease of use of the present linear surgical stapler. A support shaft connects the handle to the end effector. An articulation mechanism is positioned between the support shaft and the end effector permitting selective movement of the end effector relative to the support shaft.

It is also an object of the present invention to provide a surgical stapler wherein the articulation mechanism includes a ball joint coupling the end effector to the support shaft.

It is a further object of the present invention to provide a surgical stapler including a locking mechanism associated with the ball joint for permitting selective locking of the end effector in a desired orientation and selective release of the end effector for controlled movement when desired.

It is another object of the present invention to provide a surgical stapler wherein the locking mechanism includes a ball lock release tube.

It is also another object of the present invention to provide a surgical stapler wherein the ball joint includes a ball with a contoured outer surface shaped and dimensioned for engagement with a distal end of the ball lock release tube.

It is still another object of the present invention to provide a surgical stapler wherein the ball joint includes a ball with a contoured outer surface shaped and dimensioned to lock with the distal end of the ball lock release tube, the contouring of the ball helping to ensure frictional engagement between the ball and the distal end of the ball lock release tube.

It is also a further object of the present invention to provide a surgical stapler wherein the articulation mechanism includes multiple articulation joints.

It is yet a further object of the present invention to provide a surgical stapler wherein the multiple articulation joints are actuated by a gear and strap rotation mechanism.

It is also an object of the present invention to provide a surgical stapler wherein the gear and strap rotation mechanism includes an articulation knob linked to a gear, which is in turn linked to first and second control rod, which are linked to a rotation gear that drives a fixed gear secured to the end effector.

It is also another object of the present invention to provide a surgical stapler wherein the multiple articulation joints are actuated by a cable linked to a gearing structure attached to the end effector.

It is also a further object of the present invention to provide a surgical stapler wherein the end effector is releasably secured to the support shaft.

It is another object of the present invention to provide a surgical stapler wherein a bayonet type lock between the end effector and the support shaft permits selective release.

It is still another object of the present invention to provide a surgical stapler wherein the end effector is curved.

It is yet another object of the present invention to provide a surgical stapler wherein the end effector is a surgical fastening assembly that includes a cartridge module and a supporting structure.

It is a further object of the present invention to provide a surgical stapler wherein the cartridge module includes a cartridge housing coupled to an anvil.

It is also an object of the present invention to provide a surgical stapler including a drive cable extending from the handle to the end effector for actuation of the cartridge module.

It is also another object of the present invention to provide a surgical stapler wherein the cartridge housing includes a recess shaped and dimensioned for slideably receiving a push collar within which a threaded distal end of the drive cable is engaged for movement of the cartridge housing and push collar toward the anvil.

It is also a further object of the present invention to provide a surgical stapler wherein the push collar is selectively released from engagement with the cartridge housing permitting continued forward movement of the push collar in a manner forcing a knife and staples with the cartridge housing toward the anvil.

It is also an object of the present invention to provide a surgical stapler further including an anti-back up mechanism preventing undesired rearward movement of the cartridge housing.

It is another object of the present invention to provide a surgical stapler including a flexible retaining pin drive cable actuating a retaining pin.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 11, 12, 13 and 14 show various views of the ball joint employed in accordance with the embodiment shown with reference to FIG. 1.

FIGS. 15 and 16 show yet another embodiment in accordance with the present invention.

FIGS. 17 and 18 disclose still another embodiment in accordance with a preferred embodiment of the present invention.

FIGS. 19, 20 and 21 show a detachment mechanism for use in accordance with the present invention.

FIGS. 22 and 23 show a system providing for rotation of the end effector in accordance with the present invention.

DESCRIPTION OF THE PREFERRED EMBODIMENTS

Figure 1:
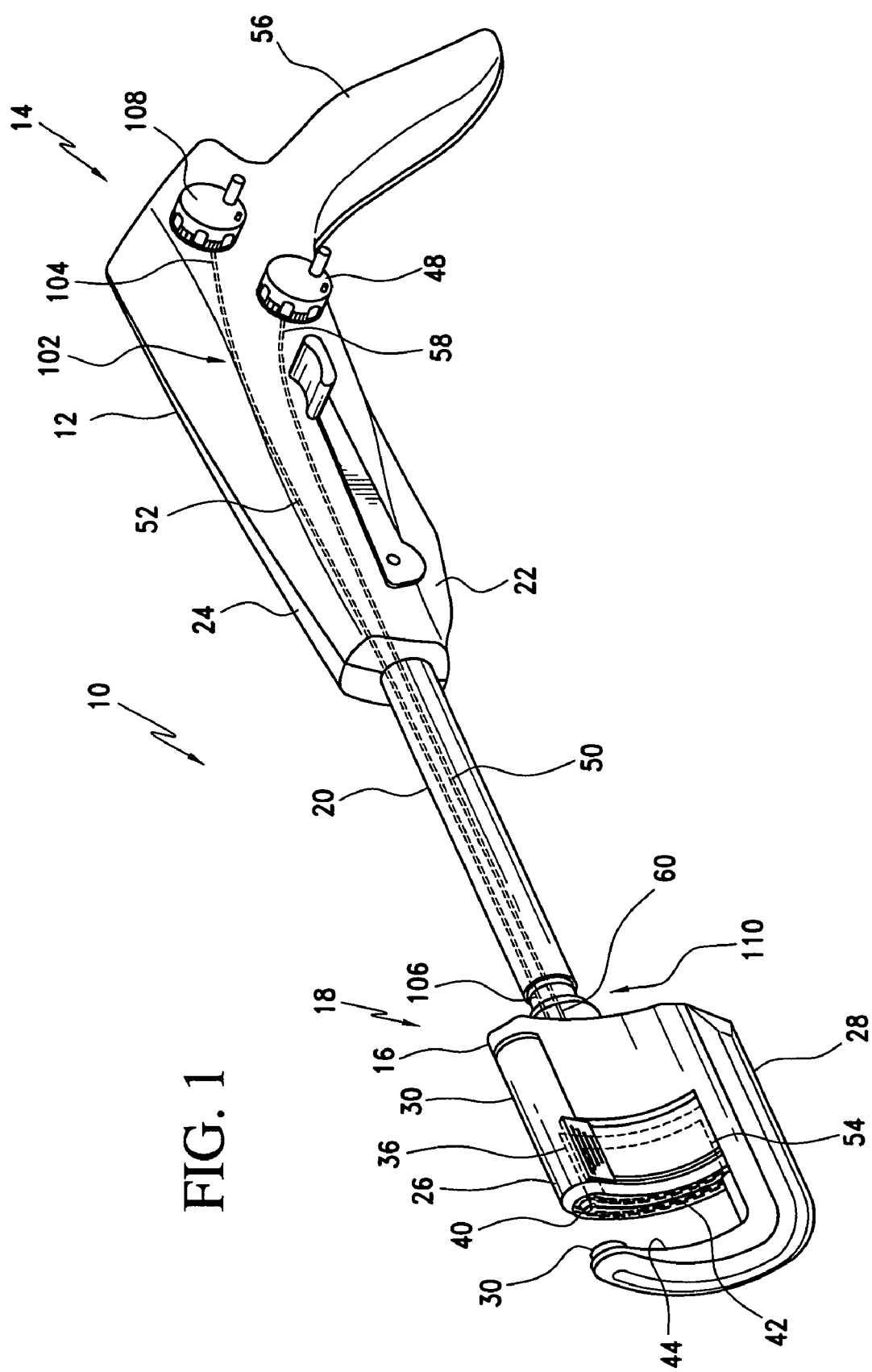
FIG. 1 is a detailed perspective view showing a surgical stapler in accordance with the present invention.
Figure 2:
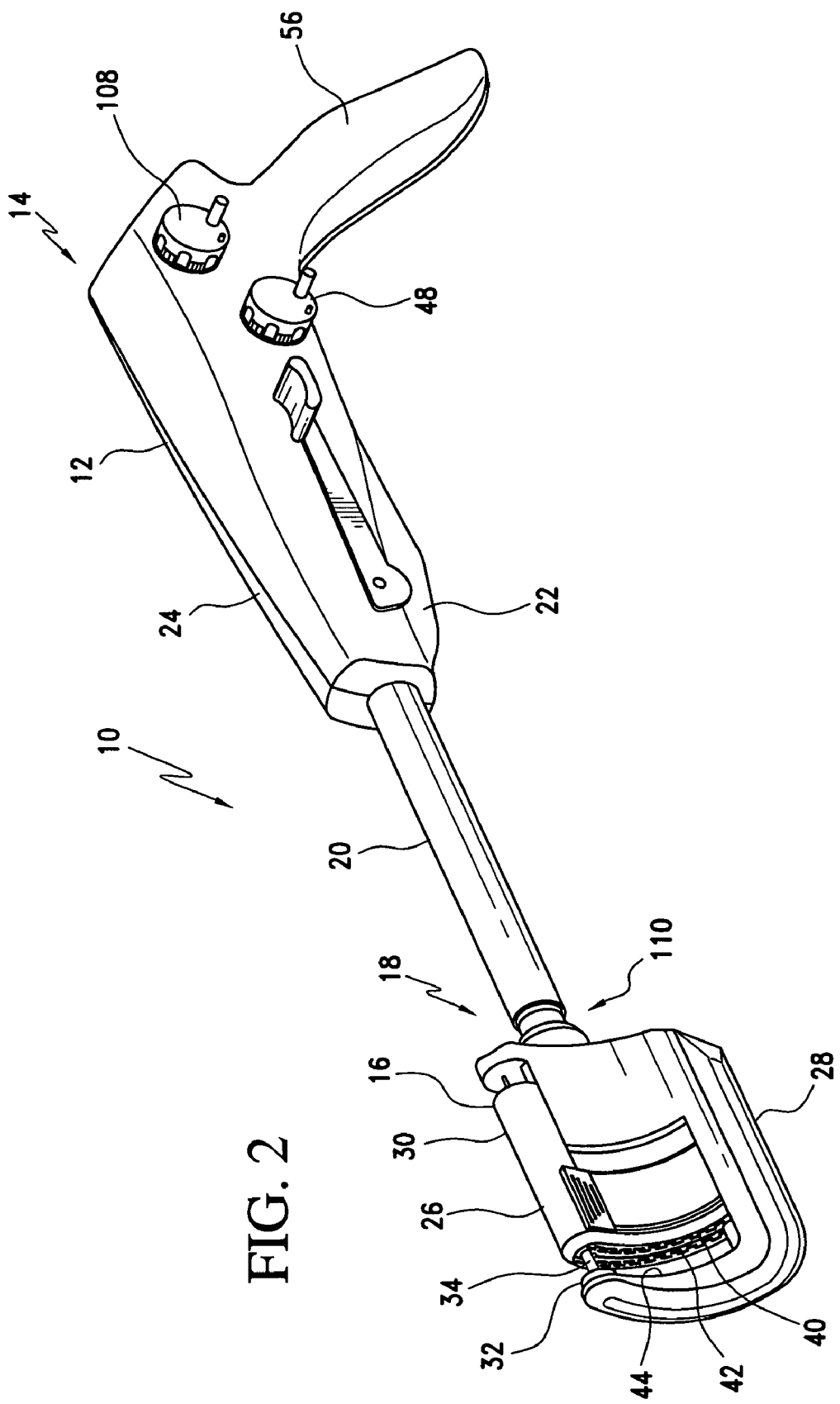
FIG. 2 is a perspective view of the surgical stapler shown in FIG. 1 with the cartridge module actuated.
Figure 3:
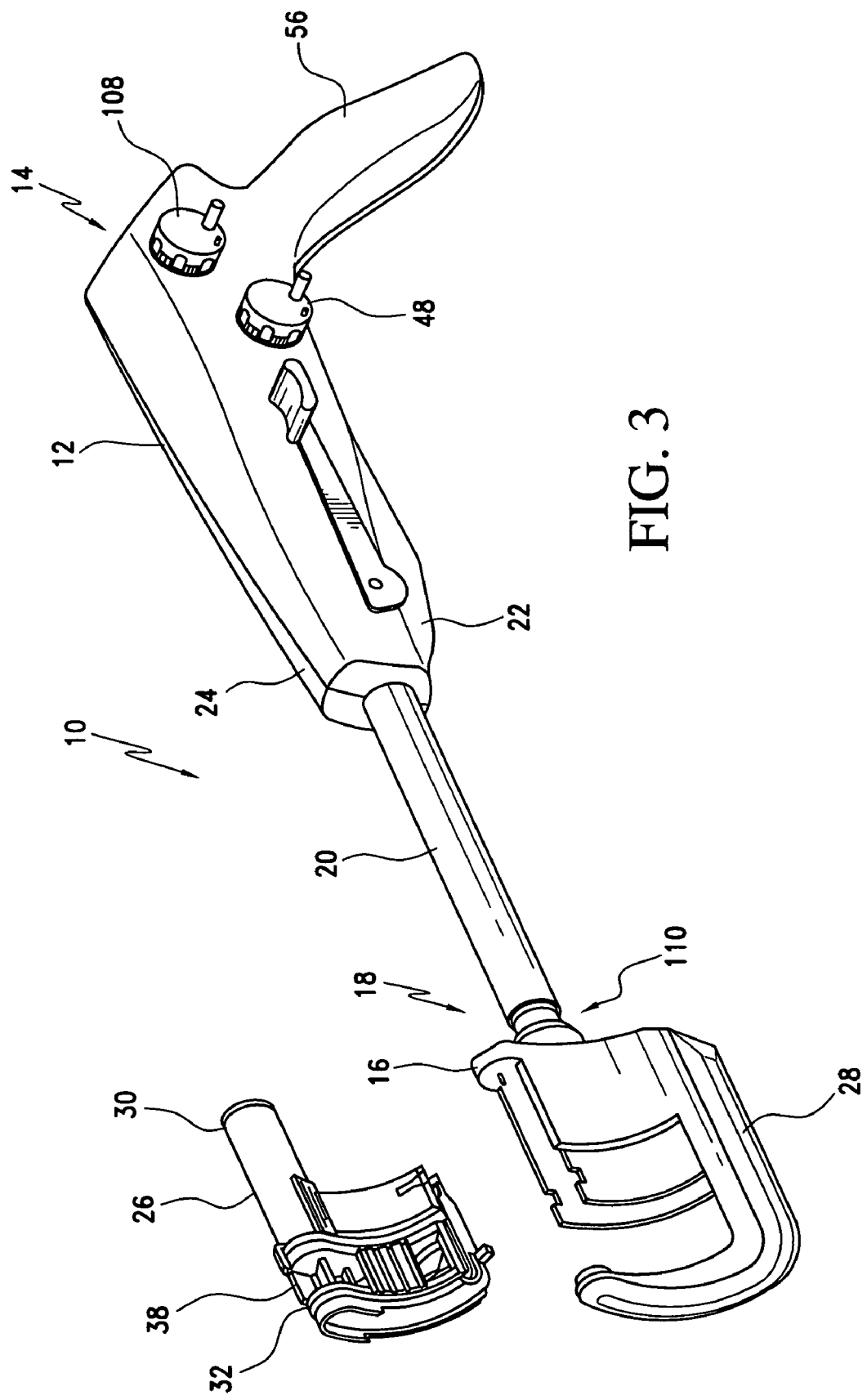
FIG. 3 is a perspective view of the surgical stapler shown in FIG. 1 with the cartridge module removed.
Figure 4:
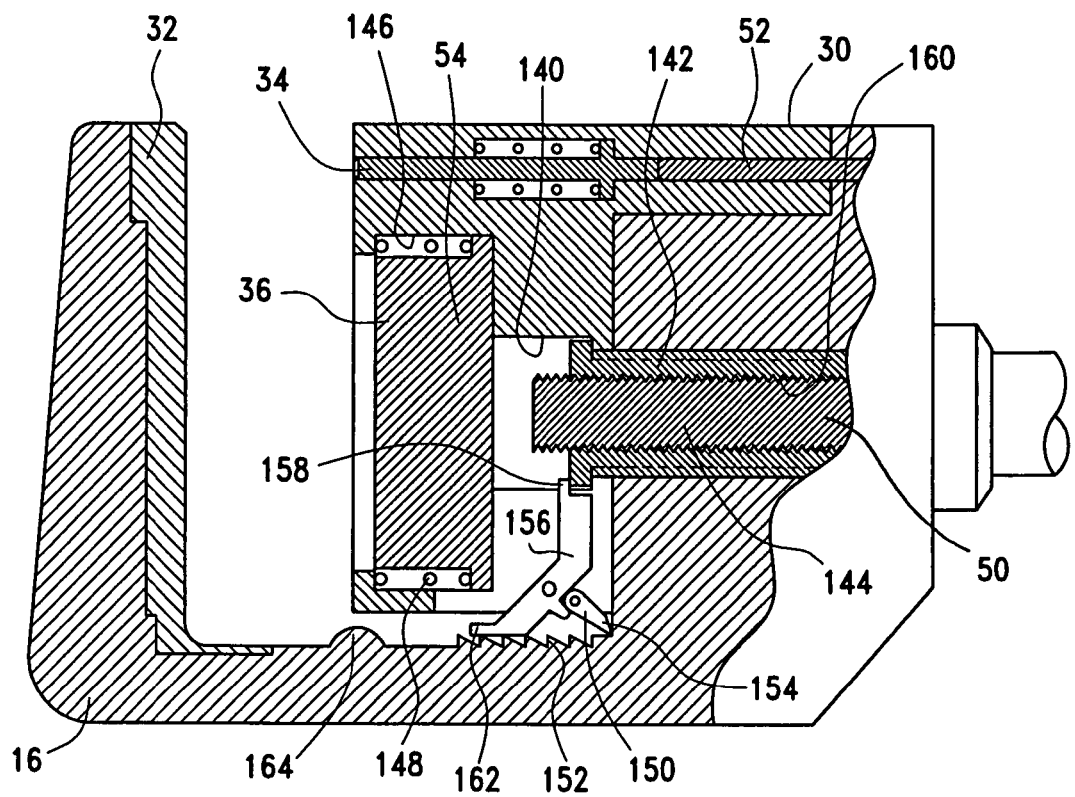
FIGS. 4, 5, 6 and 7 are cross-sectional views of the end effector showing actuation of the cartridge module.
Figure 5:
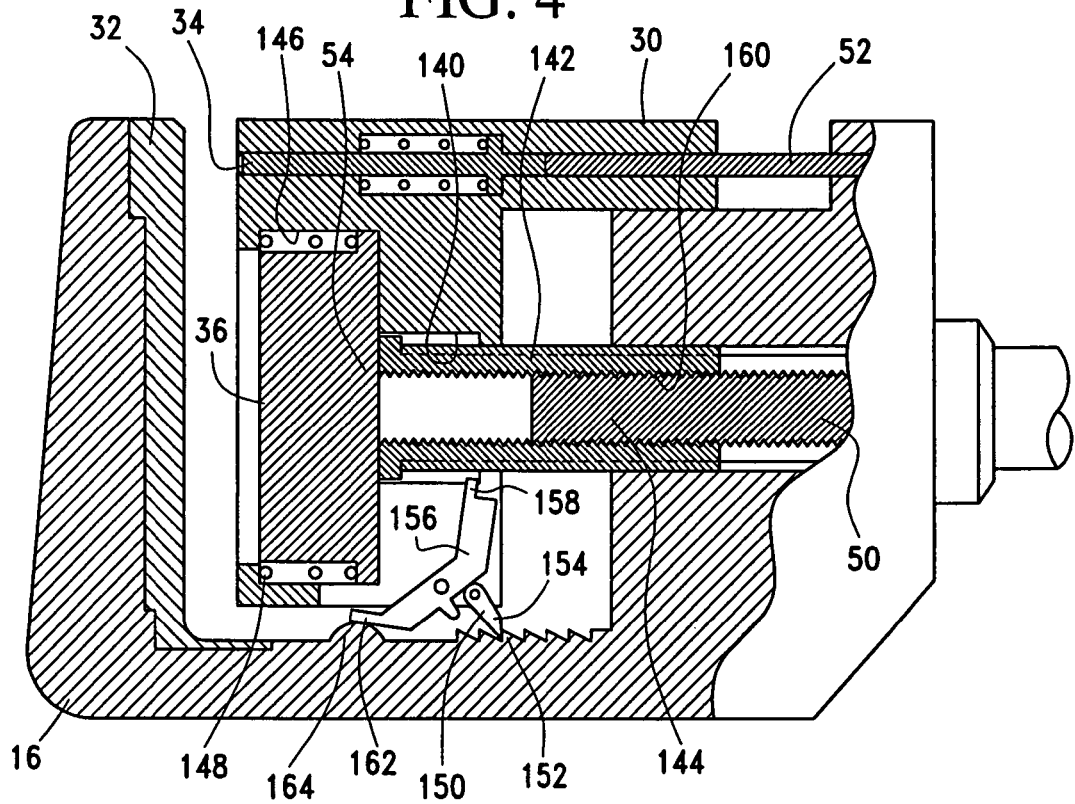
Figure 6:
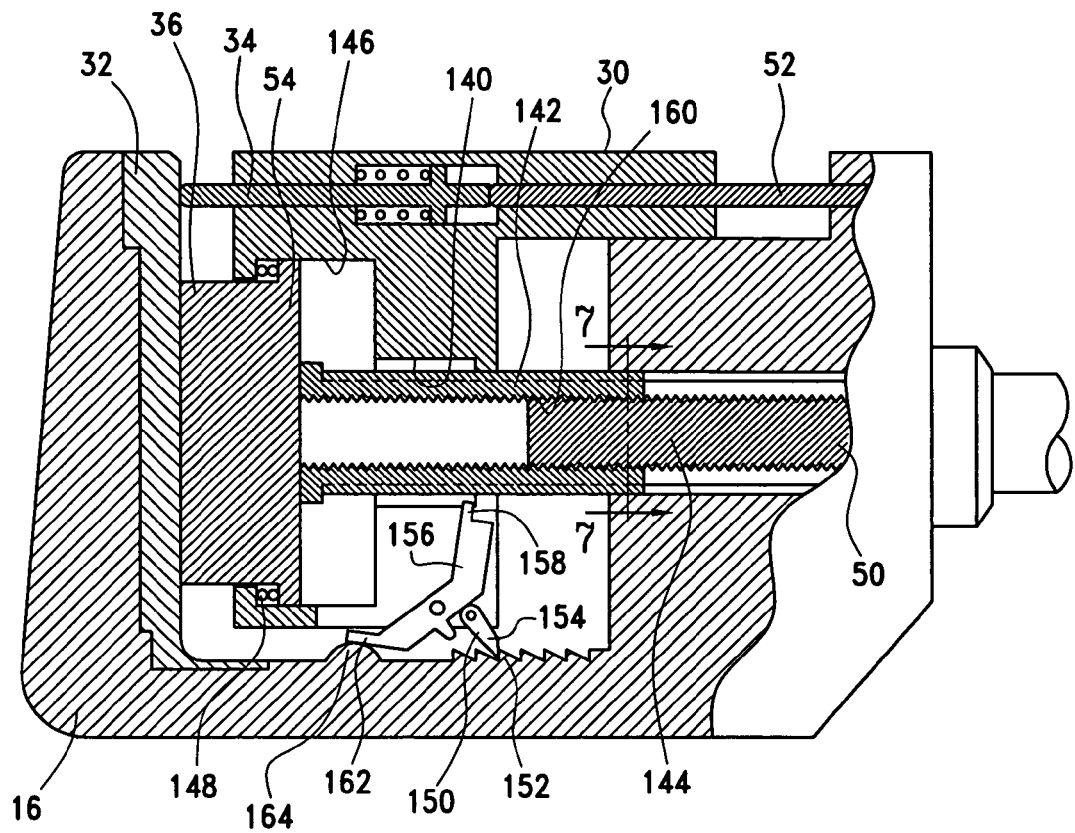
Figure 7:
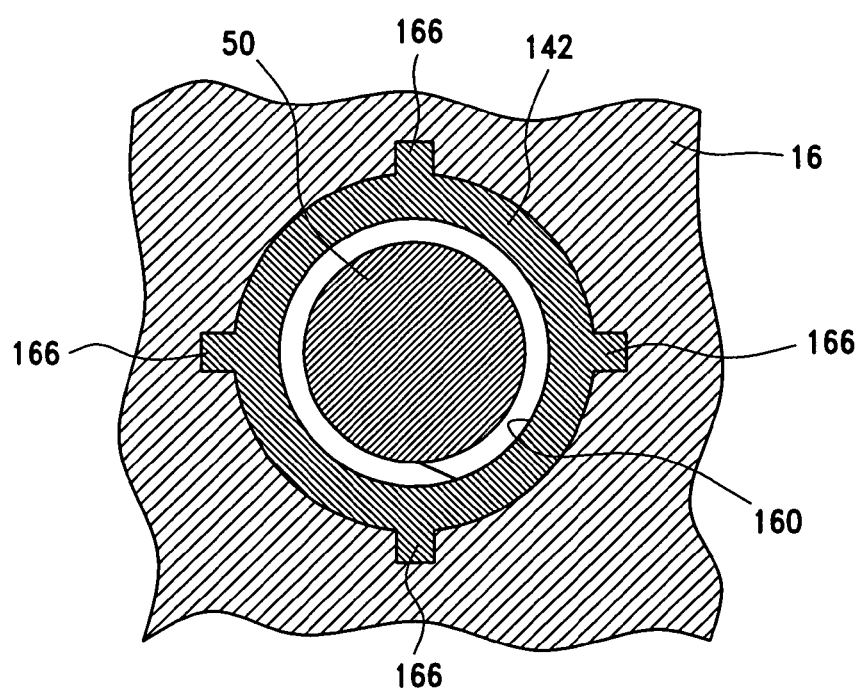

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and for teaching one skilled in the art how to make and/or use the invention.

Referring to FIGS. 1 to 10, a surgical stapling and cutting instrument, in particular, a linear surgical stapler, 10 is disclosed. The linear surgical stapler 10 is designed to staple and cut tissue. The linear surgical stapler 10 has a handle 12 at a proximal end 14 and an end effector 16 at an opposite distal end 18. As is discussed below in substantial detail, the end effector 16 is supported such that it may be selectively articulated to improve access to tissue requiring treatment and ease of use of the present linear surgical stapler 10.

The end effector 16 is curved in accordance with a preferred embodiment of the present invention, although those skilled in the art will appreciate end effectors of various shapes may be employed without departing from the spirit of the present invention. A support shaft 20 connects the handle 12 to the end effector 16 of the instrument. In accordance with a preferred embodiment of the present invention, the handle 12 has right and left-hand shrouds 22, 24. The handle 12 also has a body portion to grip and maneuver the linear surgical stapler 10.

The end effector 16 is a surgical fastening assembly that includes a cartridge module 26 and a C-shaped supporting structure 28. The term "C-shaped" is used throughout the specification to describe the concave nature of the supporting structure 28 and the cartridge module 26. The C-shaped construction facilitates enhanced functionality and the use of the term C-shaped in the present specification should be construed to include a variety of concave shapes which would similarly enhance the functionality of the surgical stapling and cutting instrument. The end effector 16 is shaped and dimensioned to receive the cartridge module 26. The end effector 16 also includes a safety lockout mechanism for preventing the firing of a previously fired cartridge module. While the present end effector is disclosed below as being adapted for use in conjunction with a replaceable cartridge module having various components, the concepts underlying the present invention could be applied to a variety of end effector and cartridge module constructions without departing from the spirit of the present invention.

As will become apparent based upon the following disclosure, the present linear surgical stapler 10 is designed as a multiple firing device with a replaceable cartridge module 26. However, it should be understood that many of the underlying concepts of the present invention may be equally applied in single firing devices without departing from the spirit of the present invention.

More particularly, and in accordance with a preferred embodiment, the cartridge module 26 includes a cartridge housing 30 coupled to an anvil 32. The cartridge module 26 also includes a retaining pin 34, a knife 36, a removable retainer 38, a tissue contacting surface 40 which displays a plurality of staple-containing slots 42 in staggered formation in one or more rows (that is, staple lines) on either side of the knife 36. Staples (not shown) are fired from the cartridge housing 30 against a staple-forming surface 44 of the anvil 32 that faces the tissue-contacting surface 40 of the cartridge housing 30.

As will be discussed below in greater detail, the cartridge module 26 operates in the following manner. Once the cartridge module 26 is properly loaded, a crank 48 mounted along the handle 12 is actuated to rotate a drive cable 50, actuating the end effector 16 of the linear surgical stapler 10. The initial actuation of the drive cable 50 causes initial closure of the cartridge module 26. That is, the drive cable 50 causes the cartridge housing 30 to move from its fully opened position to an intermediate position between the open and closed positions. Once the cartridge housing 30 is moved to its intermediate position, a retaining pin drive cable 52 is actuated to move the retaining pin 34 forward from the cartridge housing 30 through an opening in the anvil 32. In this position, tissue which has been placed between the cartridge housing 30 and the anvil 32 can be properly positioned, and the retention of the tissue between the cartridge housing 30 and the anvil 32 is assured. When the drive cable 50 has been actuated to move the cartridge housing 30 to its intermediate position, the cartridge housing 30 and anvil 32 are correspondingly positioned in their tissue retaining positions.

As the drive cable 50 is further rotated in a manner driving the cartridge housing 30 forward, the tissue contacting surface 40 of the cartridge housing 30 and the staple-forming surface 44 of the anvil 32 are adjacent to each other, and the properly positioned and retained tissue is consequently fully clamped. Thereafter, the drive cable 50 is further rotated driving the staple driver 54 forward in a manner firing the staples and moving the knife 36 forward to cut the tissue.

The handle 12 of the linear surgical stapler 10 includes a handgrip 56 that the surgeon grasps with the palm of his hand. The handgrip 56 is composed of a right hand shroud 24 and a left hand shroud 22. The previously discussed crank 48, or other user actuated mechanism, for driving the firing mechanism of the present surgical stapling and cutting instrument 10 is accessed by a user along the handle 12 of the linear surgical stapler 10.

Since the articulation of the end effector 16 relative to the support shaft 20 and handle 12 necessitates a firing mechanism capable of bending with the articulation of the end effector 16, and as briefly discussed above, the handle 12 is linked to the end effector 16 via a flexible drive cable 50. More particularly, the firing mechanism of the present linear surgical stapler is actuated by a flexible drive cable 50 having a proximal end 58 and a distal end 60. The drive cable 50 actuates movement of the cartridge housing 30, driver 54 for the staples and the knife 36 in a controlled manner. In particular, the drive cable 50 extends from the handle 12 of the linear surgical stapler 10 to the cartridge housing 30, driver 54 for the staples and the knife 36 located at the end effector 16 of the linear surgical stapler 10.

A user engageable interface 48 is provided at the proximal end 58 of the drive cable 50. For example, and in accordance with a preferred embodiment, the user engageable interface is a crank 48 which may be selectively rotated by the user to apply torque along the length of the drive cable 50 which is ultimately converted to linear movements of cartridge housing 30, driver 54 for the staples and knife 36.

With regard to the distal end 60 of the drive cable 50, it threadingly engages the cartridge housing 30, driver 54 for the staples and the knife 36 in a manner allowing one to linearly move these elements upon controlled rotation of the drive cable 50. As such, by rotating the drive cable 50, the cartridge housing 30, driver 54 for the staples and knife 36 are moved toward the anvil 32 in a controlled manner allowing one to staple and cut tissue.

More particularly, and with reference to FIGS. 4, 5, 6 and 7, operation of the cartridge housing 30 in driving staples and the knife 36 is shown. In accordance with a preferred embodiment, the cartridge housing 30 includes a recess 140 shaped and dimensioned for receiving a push collar 142 within which a threaded distal end 144 of the drive cable 50 is engaged for movement thereof in a manner discussed below in greater detail. As will be discussed below in greater detail, the push collar 142 is held within the recess 140 for controlled movement relative thereto.

When the drive cable 50 is rotated in a predetermined direction, the cartridge housing 30 and push collar 142 are moved forward toward the anvil 32. The staples and knife 36 are similarly driven forward toward the anvil 32. Continued rotation of the drive cable 50 causes the cartridge housing 30 to move even closer to the anvil 32. Once the cartridge housing 30 is relatively close to the anvil 32, the push collar 142 is released from engagement with the cartridge housing 30 permitting continued forward movement of the push collar 142 and driver 54 in a manner forcing the knife 36 and staples toward the anvil 32.

More particularly, the driver 54 is mounted within a recess 146 formed in the cartridge housing 30. The driver 54 is biased by a spring 148 in the direction away from the anvil 32 and toward the push collar 142. As such, when the push collar 142 is released and permitted to freely move relative to the cartridge housing 30, the driver 54 is pushed toward the anvil 32, against the bias of the spring 148, until the staples and knife 36 are driven through the tissue into the anvil 32 where the staples are bent over in a manner securing them to the tissue.

As those skilled in the art will certainly appreciate, it is important the cartridge housing 30 not be prone to accidental back up. As such, an anti-back up mechanism is provided. The anti-back up mechanism generally includes an anti-back up pawl 150 shaped and dimensioned to engage teeth 152 formed along the end effector 16 in a manner preventing rearward movement of the cartridge housing 30. In particular, the anti-back up pawl 150 is a longitudinally extending member 154 pivotally secured to the cartridge hosing 30 and biased for rotation toward the wall of the end effector 16. The anti-back up pawl 150 is biased by a spring (not shown) toward the wall of the end effector 16 such that it will engage the teeth 152 formed therein to prevent backup thereof.

As briefly discussed above, movement of the driver 54 is achieved by the provision of a push collar 142 within the recess 140 of the cartridge housing 30. The push collar 142, when maneuvered in conjunction with the drive cable 50 and a drive pawl 156, allows one to push the driver 54 forward against the resistance of the spring 148 biasing the driver 54 to a closed position. More particularly, the drive pawl 156 is pivotally mounted on the cartridge housing 30 for movement between a locking position (see FIG. 4) and a release position (see FIGS. 5 and 6). In the locking position, the drive pawl 156 has a first end 158 which engages the push collar 142 formed within the recess 140 of the cartridge housing 30. When engaging the push collar 142, the drive pawl 156 prevents movement of the push collar 142 relative to the cartridge housing 30. The push collar 142 includes internal threads 160 in which the distal end 144 of the drive cable 50 rides. As such, and while the drive pawl 156 is securely holding the push collar 142 in position, the entire cartridge housing 30 is moved forward upon rotation of the drive cable 50.

When the cartridge housing 30 reaches a predetermined point relative to the anvil 32, the second end 162 of the drive pawl 156 is engaged by a ramp 164 along the end effector 16 which rotates it in a counterclockwise direction moving the first end 158 of the drive pawl 156 from its engaged locking position with the push collar 142. As such, the push collar 142 is permitted to move distally relative to the cartridge housing 30 as the drive cable 50 is rotated therein. Rotation of the push collar 142 relative to the drive cable 50 is prevented by the provision of splines 166 extending from the push collar and into the cartridge housing 30. As the drive cable 50 is rotated, with the drive pawl 156 disengaged from the push collar 142, the push collar 142 is pushed toward the anvil 32, thereby pushing the driver 54 against the resistance of the spring 148, toward the anvil 32 in a manner forcing the staples and knife through the tissue.

In accordance with a preferred embodiment of the present invention, strands and cables are ideal for use in construction of the drive cable. The structures provide greater strength and flexibility than a single wire filament can achieve. These highly engineered products often utilize complex constructions or processes to enhance fatigue life, strength, flexibility, torque, stiffness and smoothness. The drive cable may range from ultra fine or miniature strands with diameters below approximately 0.003" to cables up to approximately 0.125" in diameter.

Figure 8:
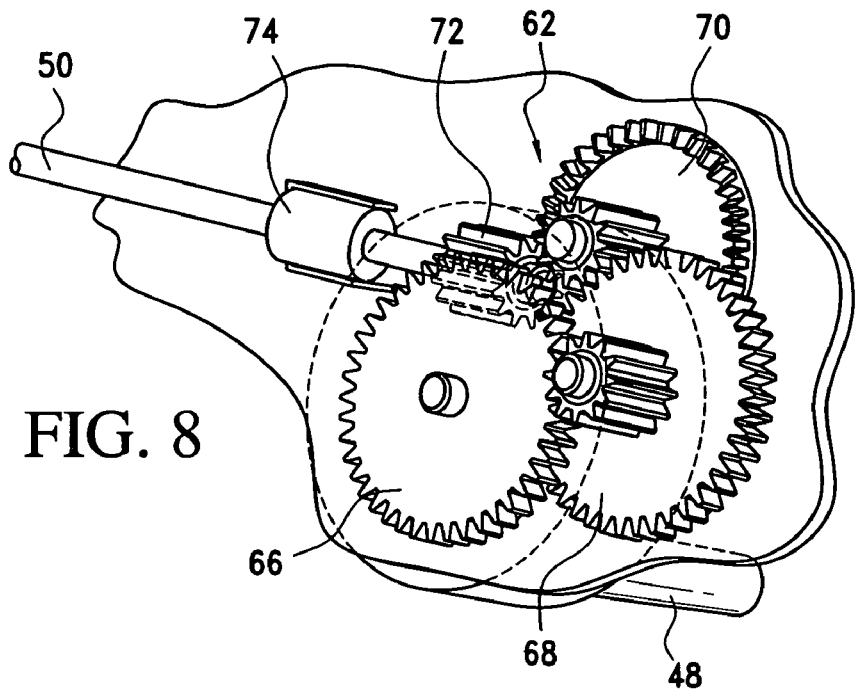
FIG. 8 is a detailed view showing the transmission mechanism in accordance with a preferred embodiment of the present invention.
Figure 10:
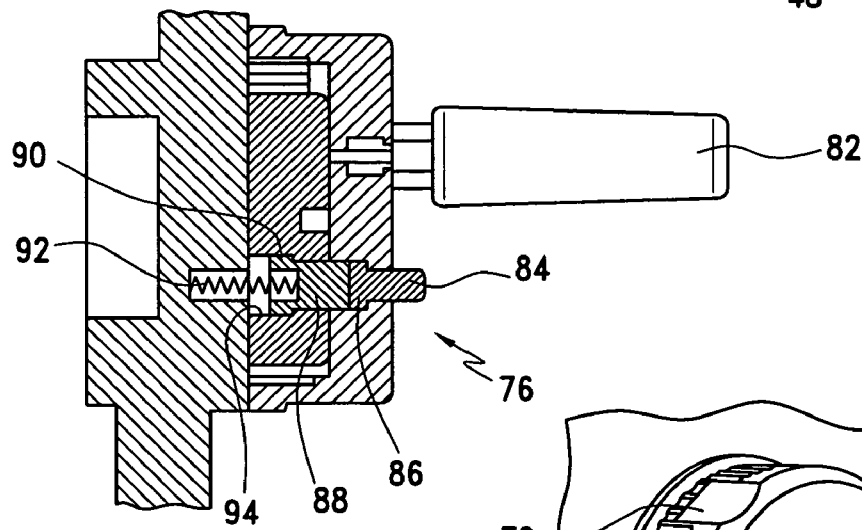
FIG. 10 is a cross-sectional view of the transmission mechanism.
Figure 9:
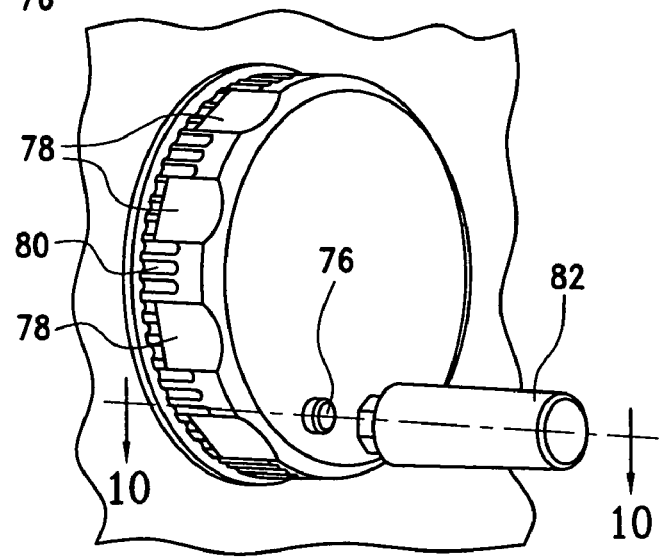
FIG. 9 is a perspective view of the crank utilized in accordance with the embodiment shown in FIG. 8.

More particularly, and with reference to FIGS. 8, 9 and 10, the crank 48, used to rotate the drive cable 50, is coupled to a transmission 62. More particularly, the transmission 62 includes an input spur gear 66 which is coupled to the crank 48, a step-up spur gear 68 coupled to the input spur gear 66, and a crown gear 70 which is coupled to the step-up spur gear 68. The crown gear 70 engages a pinion 72 coupled to the drive cable 50 for rotation thereof.

According to the presently preferred embodiment, an energy storing flywheel 74 is coupled to the drive cable 50. Alternatively, the flywheel 74 and drive cable 50 could be a single molded part. The flywheel 74 smoothes the operation of the crank 48 which would otherwise require the application of increasing force through its rotation, as in the beginning of its rotation, the drive cable 48 is causing the advancement of a firing mechanism. Those skilled in the art will appreciate that in order to be effective, the flywheel 74 is preferably provided with a relatively large rotational mass for energy storage. When the flywheel 74 is spun (rotated) by rotation of the crank 48, a certain amount of energy is invested which increases the kinetic energy of the flywheel 74. Some of this energy is lost over time to friction. However, some of the energy used to spin the flywheel 74 is stored in the form of kinetic energy. Later, it is possible to retrieve this energy through direct mechanical translation. In the case of the present invention, when the crank 48 is first rotated, the drive cable 50 offers little resistance and most of the energy applied to the crank 48 is used to put the flywheel 74 in rotation. Near the end of the crank's rotation, torsional resistance is built up by the drive cable 50 because it is near the end of the cycle. At this point, the kinetic energy in the flywheel 74 is released and eases the remainder of the crank cycle. Preferably, according to the invention, the flywheel 74 is chosen so that the force which is applied to the crank 48 is substantially even (e.g., does not change by more than 25%) over the entire movement of the crank 48 necessary to dispense a single clip.

As seen best in FIGS. 9 and 10, the crank 48 is provided with a detent lock 76 which must be released before the crank 48 can be turned and which automatically locks the crank 48 after one rotation. Preferably, the crank 48 is also provided with a ratchet mechanism (not shown) which prevents it from being rotated backwards. The crank 48 is preferably provided with a lock (not shown) which prevents it from being turned until the jaws are closed. The crank 48 may also be provided with a revolution counter (not shown) which can be coupled to the input spur gear 66 and which counts the number of times the crank 48 has been rotated and thus indicates the position of the cartridge housing 30, driver 54 for the staples and the knife 36. The revolution counter may also be used to prevent the crank 48 from rotating after the firing cycle has been completed.

According to the embodiment illustrated in FIG. 9, the crank 48 has a plurality of spaced apart peripheral finger grips 78 and a knurled outer periphery 80. The crank handle 82 is optionally removable so that the crank 48 can be rotated like a knob if desired. The detent lock 76 includes a push button 84 having a flange 86, a lock pin 88 having a flange 90 and a spring 92. The lock pin 88 is disposed in a stepped bore 94 and is biased by the spring 92 into the stepped bore 94 in the crank 48. When the button 84 is pressed, the lock pin 88 is moved against the spring 92 and out of the bore 96, freeing the crank 48 to rotate.

According to an exemplary embodiment, the transmission 62 causes the drive cable 50 to be rotated a predetermined number of revolutions when the crank 48 is turned one revolution. The pitch of the threads 98 at the distal end 60 of the drive cable 50 results in the cartridge housing 30, driver 54 for the staples and the knife 36 advancing a predetermined distance when the crank 48 is turned one revolution. The gears and the thread pitch are selected for a particular clip length. According to the presently preferred embodiment, it is only necessary to change the crown gear (by increasing or decreasing the number of teeth) to accommodate clips of different length.

The present surgical stapler 10 is further provided with a retaining pin actuation mechanism 102. However, and considering the present invention requires flexing along the articulation joint, actuation of the retaining pin 34 is achieved through the implementation of the flexible retaining pin drive cable 52. The flexible retaining pin drive cable 52 includes a proximal end 104 and a distal end 106. The retaining pin drive cable 52 actuates movement of the retaining pin 34. In particular, the retaining pin drive cable 52 extends from the handle 12 of the linear surgical stapler 10 to the retaining pin 34 located at the end effector 16 of the linear surgical stapler 10. A user engageable interface 108 is provided at the proximal end 104 of the retaining pin drive cable 52. For example, and in accordance with a preferred embodiment, the user engageable interface is a crank 108 which may be selectively rotated by the user to apply torque along the length of the retaining pin drive cable 52.

With regard to the distal end 106 of the retaining pin drive cable 52, it threadingly engages the retaining pin 34 in a manner allowing one to move the retaining pin 34 upon controlled rotation of the retaining pin drive cable 52. As such, by rotating the retaining pin drive cable 52, the retaining pin 34 is moved toward the anvil 32 in a controlled manner allowing one to extend the retaining pin 34 across the end effector 16. Movement of the retaining pin drive cable 52 is identical to that of the drive cable 50 discussed above.

As shown with reference to FIGS. 11, 12, 13 and 14, the supporting structure 28 of the end effector 16 is attached to the support shaft 20 via a ball joint 110 positioned at the distal end 112 of the support shaft 20, which will be discussed below in greater detail. The ball joint 110 is composed of a ball 114 retained for movement within a concave recess 116 positioned at the distal end 112 of the support shaft 20 and the ball 114 is fixedly secured to the end effector 16 for movement therewith.

In accordance with a preferred embodiment of the present invention, the supporting structure 28 is formed via a single piece construction. More specifically, the supporting structure 28 is formed by extrusion, for example, of aluminum, with subsequent machining to create the supporting structure 28 disclosed in accordance with the present invention. By constructing the supporting structure 28 in this manner, multiple parts are not required and the associated cost of manufacture and assembly is substantially reduced. In addition, it is believed the unitary structure of the supporting structure 28 enhances the overall stability of the present linear surgical stapler 10. In addition, the unitary extruded structure of the supporting structure 28 provides for a reduction in weight, easier sterilization since cobalt irradiation will effectively penetrate the extruded aluminum and fewer traumas to tissue based upon the smooth outer surface achieved via extrusion.

More particularly, the end effector 16 is secured to the support shaft 20 in a manner permitting the end effector 16 to selectively move relative thereto about multiples axes. As will be discussed below in greater detail, the end effector 16 is selectively secured to the support shaft 20 for removal of the end effector 16 and reassembly thereof when the surgical stapler 10 is positioned within the patient's body.

More particularly, and as briefly discussed above, the ball joint 110 links the end effector 16 to the support shaft 20. The ball joint 110 is held at the distal end 112 of the support shaft 20 with a concave recess or socket 116 shaped and dimensioned to retain the ball 114 at the distal end 112 of the support shaft 20 while permitting rotational movement relative thereto. In this way, the ball 114 is moved relative to a socket 116 formed in the distal end 112 of the support shaft 20, resulting in controlled movement of the end effector 16 to which it is secured.

In accordance with a preferred embodiment, and with reference to FIGS. 13 and 14, the ball joint 110 is provided with a locking mechanism 118 allowing the surgeon to selectively lock the end effector 16 in a desired orientation and selectively release the end effector 16 for controlled movement when desired. In particular, a ball lock release tube 120 extends from the handle 12 to the ball joint 110. The ball lock release tube 120 is positioned for axial movement along the length of support shaft 20. As such, it may be moved from a locked position in which it is in engagement with the ball joint 110 and an unlocked position in which it is proximally positioned away from the ball joint 110.

A spring 122 is connected to the ball lock release tube 120 for biasing it to its locked position. When, however, it is desired to move the ball lock release tube 120, a release arm 124, secured to the ball lock release tube 120, is actuated to draw the ball lock release tube 120 away from the ball joint 110. When the ball lock release tube 120 is withdrawn in this manner, the ball joint 110 is free to rotate for articulation of the end effector 16 in a desired manner.

Locking of the ball joint 110 is further enhanced by providing the ball 114 with a contoured outer surface shaped and dimensioned to "lock" with the distal end 126 of the ball lock release tube 120. The contouring of the ball 114 helps to ensure frictional engagement between the ball 114 and the distal end 126 of the ball lock release tube 120.

With the foregoing in mind, the release tube 120 and the ball 114 permit relative orienting of the end effector 16. However, and in accordance with a preferred embodiment of the present invention, this articulation must be preset prior to use of the apparatus. It is, however, contemplated, orientation of the end effector 16 could be adjusted in a body cavity by releasing the release tube 120 and applying appropriate force to the end effector 16 to adjust its position. Thereafter, the release tube 120 is moved back into engagement with the ball 114 locking the end effector 16 back into its desired position.

In accordance with an alternate embodiment, and with reference to FIGS. 15 and 16, articulation of the end effector 216 is controlled by multiple articulation joints. Rotation of the end effector 216 about an axis substantially in line with the longitudinal axis of the linear surgical stapler 210 is achieved by coupling the end effector 216 to a support shaft 220 and allowing the support shaft 220 to rotate relative to the handle 212. The support shaft 220 includes a distal end 222 fixedly secured to the end effector 216 such that the end effector 216 will move with the support shaft 220. The proximal end 224 of the support shaft 220 is secured to the handle 212 for rotation relative thereto.

Controlled movement of the support shaft 220 relative to the handle 212 is facilitated by a remote articulation member 226 that acts upon the support shaft 220 in a manner causing it to rotate about a longitudinal axis of the linear surgical stapler 210 and ultimately rotate the end effector 216 about the same axis.

With regard to rotation of the end effector 216 about an axis that is perpendicular to the longitudinal axis of the linear surgical stapler 210, it is controlled by a gear and strap rotation mechanism 228. In particular, the handle 212 is provided with an articulation knob 230 linked to a gear 232, which is in turn linked to first and second control rod 234a, 234b. Similarly, the end effector 216 includes a fixed gear 236 that is linked to the other end of the control rods 234a, 234b via a rotation gear 238 at the distal end 222 of the support shaft 220. The fixed gear 236 of the end effector 216 is fixedly secured to the end effector 216, but mounted for rotation in a manner such that the end effector 216 is rotated as the rotation gear 238 is rotated. As such, and in practice, as the knob 230 is rotated the gear 232 of the handle 212 is similarly rotated, causing the control rods 234a, 234b to move and rotate the rotation gear 238 which in turn rotates the fixed gear 236 of the end effector and ultimately rotates the end effector 216. Rotation in this manner may be used to rotate the end effector 216 in both clockwise and counterclockwise directions to facilitate a wide range of orientations.

Similarly, and with reference to FIGS. 17 and 18, the control rods may be replaced with a cable 234' which actuates a gearing structure 232' attached to the end effector 216'.

Figure 19:
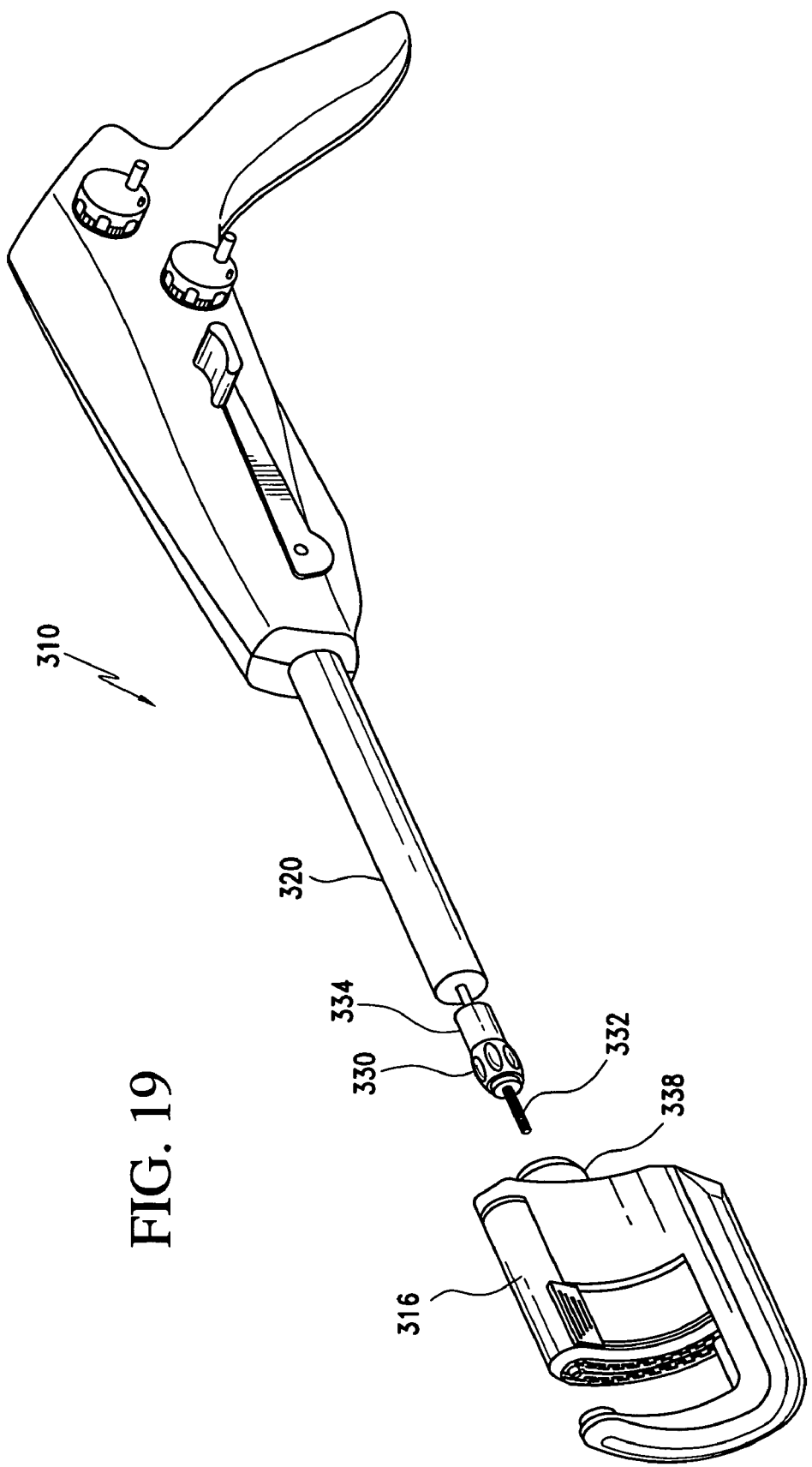

Referring to FIGS. 19, 20 and 21, and with regard to with either of the articulation mechanisms discussed above, the end effector 316 is releasably secured to the support shaft 320 in a manner permitting greater versatility in the use of the present linear surgical stapler 310. In accordance with a preferred embodiment, the support shaft 320 is provided with a bayonet type lock 334 shaped and dimensioned to engage a detachable lock head 330 secured to the proximal end 338 of the end effector 316 via a threaded shaft 332. As those skilled in the art will appreciate, to engage the bayonet type lock 334, one need only insert the locking nut 330 over the bayonet type lock 334 and rotate locking nut 330 to engage in the bayonet slot 338. Mating splines 336 are provided within the bayonet type lock 334 and lock head 330 to ensure proper positioning of the elements. As those skilled in the art will appreciate, the connection described above will be provided with a central passageway to allow for passage of control cables and other mechanism required for actuation of the end effector.

In accordance with an alternate to the those embodiments previously discussed, and with reference to FIG. 22, the ball joint disclosed with reference to FIGS. 11, 12, 13 and 14 may be combined with a rotation shaft 480 extending through a passageway 482 formed in the ball joint 410 and to the end effector 416. With the rotation shaft 480 fixedly secured within the end effector 416 rotation of the rotation shaft 480 will cause rotary movement of the end effector 416 about the longitudinal axis of the support shaft 420. Rotation in this manner is facilitated by providing bearings 484 between the ball joint 410 and the support shaft 420 such that the ball joint 410 may similarly rotate when the rotation shaft 480 is actuated.

In accordance with yet a further embodiment, and with reference to FIG. 23, the embodiment disclosed above may be simplified with the removal of the ball joint 510 where one only wishes to provide rotary adjustment of the end effector 516 about the longitudinal axis of the support shaft 520. Motion of the end effector 516 relative to the support shaft 520 is facilitated by the inclusion of bearings 584 between the proximal end shaft 586 of the end effector 516 and the distal end 588 of the support shaft 520, wherein the proximal end shaft 586 of the end effector 516 is shaped and dimensioned to fit within the support shaft 520.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An articulating surgical stapler having a proximal end and a distal end, comprising:
   a handle at the proximal end and an end effector at the distal end for selective articulation to improve access to tissue requiring treatment and ease of use of the articulating surgical stapler;
   a support shaft connects the handle to the end effector, wherein the end effector is a surgical fastening assembly that includes a supporting structure and a cartridge module, and a rotary drive cable links the handle to the end effector for actuation of the cartridge module as the cable rotates about a length of the drive cable; and
   an articulation mechanism positioned between the support shaft and the end effector permitting selective movement of the end effector relative to the support shaft, wherein the articulation mechanism includes a ball joint coupling the end effector to the support shaft and a locking mechanism associated with the ball joint for permitting selective locking of the end effector in a desired orientation and selective release of the end effector for controlled movement when desired, wherein the locking mechanism includes a ball lock release tube, the ball lock release tube being positioned for axial movement relative to the support shaft for selective movement from a locked position in which the ball lock release tube is in engagement with the ball joint and an unlocked position in which the ball lock release tube is positioned away from the ball joint.

2. The surgical stapler according to claim 1, wherein the ball joint includes a ball with a contoured outer surface shaped and dimensioned for engagement with the distal end of the ball lock release tube.

3. The surgical stapler according to claim 1, wherein the ball joint includes a ball with a contoured outer surface shaped and dimensioned to lock with the distal end of the ball lock release tube, the contouring of the ball helping to ensure frictional engagement between the ball and the distal end of the ball lock release tube.

4. The surgical stapler according to claim 1, wherein the cartridge module is composed of a cartridge housing and an anvil, and the rotary drive cable links the handle to the end effector for actuation of the cartridge module causing the cartridge housing to move forward toward the anvil and firing the cartridge module as the drive cable rotates about its length.

5. An articulating surgical stapler having a proximal end and a distal end, comprising:
   a handle at the proximal end and an end effector at the distal end for selective articulation to improve access to tissue requiring treatment and ease of use of the articulating surgical stapler;
   a support shaft connects the handle to the end effector, wherein the end effector is a surgical fastening assembly that includes a supporting structure and a cartridge module composed of a cartridge housing and an anvil, and a rotary drive cable links the handle to the end effector for actuation of the cartridge module causing the cartridge housing to move forward toward the anvil and firing the cartridge module as the cable rotates about a length of the drive cable;
   an articulation mechanism positioned between the support shaft and the end effector permitting selective movement of the end effector relative to the support shaft, wherein the articulation mechanism includes multiple articulation joints providing for rotation of the end effector relative to the support shaft about an axis substantially in line with a longitudinal axis of the linear surgical stapler and providing for rotation of the end effector relative to the support shaft about an axis perpendicular to the longitudinal axis of the surgical stapler; and
   further including a gear and strap rotation mechanism providing for rotation of the end effector about an axis perpendicular to the longitudinal axis of the surgical stapler.

6. The surgical stapler according to claim 5, wherein the gear and strap rotation mechanism includes an articulation knob linked to a gear, which is in turn linked to first and second control rods, which are linked to a rotation gear that drives a fixed gear secured to the end effector.

* * * * *